US00PP37559P2

(12) United States Plant Patent
van Swieten

(10) Patent No.: US PP37,559 P2
(45) Date of Patent: Aug. 4, 2026

(54) ***PHALAENOPSIS* PLANT NAMED 'PHA177551'**

(50) Latin Name: *Phalaenopsis hybrida*
Varietal Denomination: PHA177551

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/316,554

(22) Filed: Sep. 2, 2025

(51) Int. Cl.
*A01H 5/02* (2018.01)
*A01H 5/12* (2018.01)
*A01H 6/62* (2018.01)

(52) U.S. Cl.
USPC ..... Plt./311
CPC ..... *A01H 6/62* (2018.05); *A01H 5/02* (2013.01); *A01H 5/12* (2013.01)

(58) Field of Classification Search
USPC ..... Plt./311
See application file for complete search history.

*Primary Examiner* — Susan Mccormick Ewoldt
(74) *Attorney, Agent, or Firm* — C. Anne Whealy

(57) ABSTRACT

A new and distinct cultivar of *Phalaenopsis* plant named 'PHA177551', characterized by its upright plant habit; moderately vigorous growth habit and moderate growth rate; strong flowering stems; freely flowering habit with typically two inflorescences developing per plant, each inflorescence with numerous flowers; medium to broad white-colored flowers; and good postproduction longevity.

2 Drawing Sheets

Figure 1:
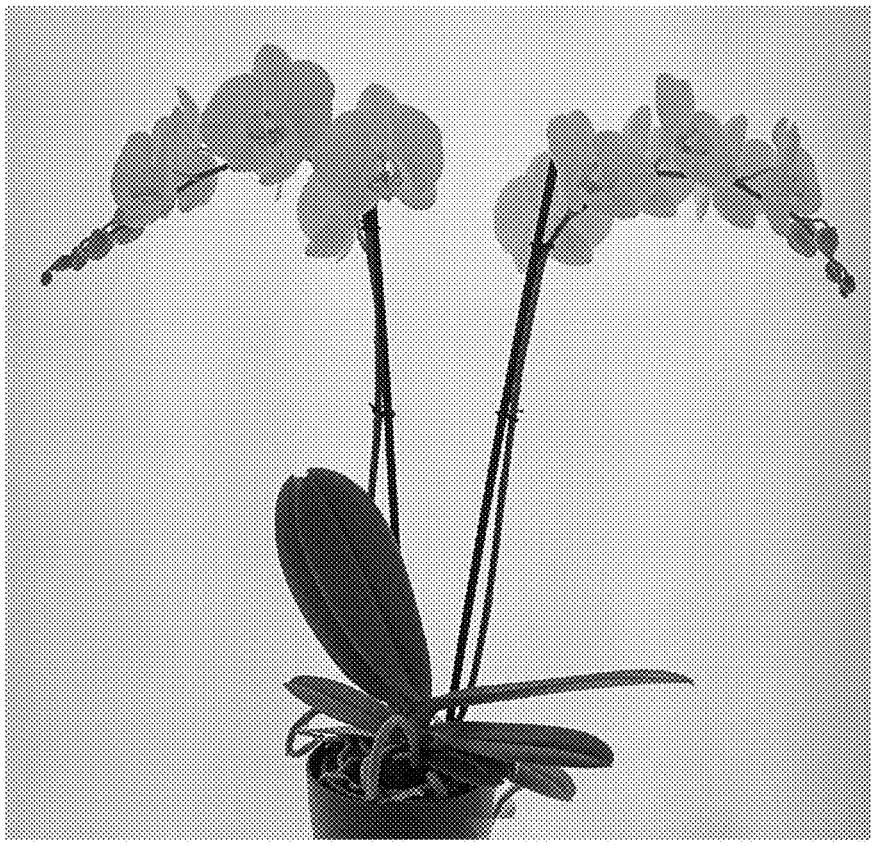

Botanical designation: *Phalaenopsis hybrida.*
Cultivar Denomination: 'PHA177551'.

A European Community Plant Breeder's Rights application for the instant plant was filed by the Applicant/Assignee of the instant application, Anthura B.V. of Bleiswijk, The Netherlands on Aug. 14,2024, application No. 2024/1898. Foreign priority is not claimed to this application.

BACKGROUND OF THE INVENTION

The present invention relates to a new and distinct cultivar of *Phalaenopsis* plant, botanically known as *Phalaenopsis hybrida*, commonly referred to as a *Phalaenopsis* or Moth Orchid and hereinafter referred to by the name 'PHA177551'.

The new *Phalaenopsis* plant is a product of a planned breeding program conducted by the Inventor in Bleiswijk, The Netherlands. The objective of the breeding program is to develop new freely flowering *Phalaenopsis* plants with flowers with unique patterns and coloration.

The new *Phalaenopsis* plant originated from a cross-pollination in July 2017 in Bleiswijk, The Netherlands of *Phalaenopsis hybrida* 'PHALHORDIN', disclosed in U.S. Plant Pat. No. 33,096, as the female, or seed, parent with a proprietary breeding selection of *Phalaenopsis hybrida* identified as code No. 07-000001-5280, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in March 2020.

Asexual reproduction of the new *Phalaenopsis* plant by in vitro meristem propagation in a controlled environment in Bleiswijk, The Netherlands since March 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA177551'. These characteristics in combination distinguish 'PHA177551' as a new and distinct *Phalaenopsis* plant:

1. Upright plant habit.
2. Moderately vigorous growth habit and moderate growth rate.
3. Strong flowering stems.
4. Freely flowering habit with typically two inflorescences developing per plant, each inflorescence with numerous flowers.
5. Medium to broad white-colored flowers.
6. Good postproduction longevity.

Plants of the new *Phalaenopsis* can be compared to plants of the female parent, 'PHALHORDIN'. Plants of the new *Phalaenopsis* differ primarily from plants of 'PHALHORDIN' in the following characteristics:

1. Leaves of plants of the new *Phalaenopsis* are obovate to elliptic-obovate in shape whereas leaves of plants of 'PHALHORDIN' are elongated linear.
2. The dorsal sepal apices of plants of the new *Phalaenopsis* are obtuse whereas the dorsal sepal apices of plants of 'PHALHORDIN' are emarginate.

Plants of the new *Phalaenopsis* can be compared to plants of the male parent selection. Plants of the new *Phalaenopsis* differ primarily from plants of the male parent selection in the following characteristics:

1. Leaves of plants of the new *Phalaenopsis* are horizontal to slightly drooping whereas leaves of plants of the male parent selection are semi-erect to horizontal.
2. The lateral lobes of the labella of plants of the new *Phalaenopsis* are not as inwardly curved as the lateral lobes of the labella of plants of the male parent selection.

Plants of the new *Phalaenopsis* can be compared to plants of *Phalaenopsis hybrida* 'PHA773779', disclosed in U.S. Plant Pat. No. 35,381. In side-by-side comparisons, plants of the new *Phalaenopsis* differ primarily from plants of 'PHA773779' in the following characteristics:

1. Plants of the new *Phalaenopsis* are shorter than plants of 'PHA773779'.
2. Leaves of plants of the new *Phalaenopsis* are obovate to elliptic-obovate in shape whereas leaves of plants of 'PHA773779' are oblong.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA177551' grown in a container.

Figure 2:
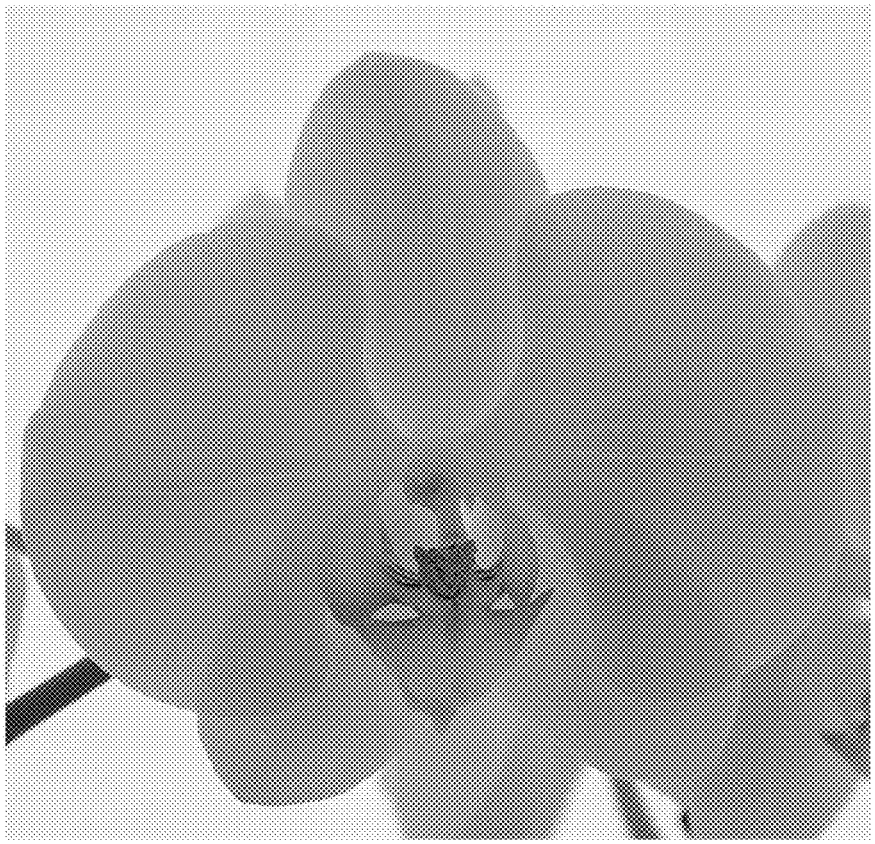

The photograph on the second sheet (FIG. 2) is a close-up view of a typical flower of 'PHA177551'.

DETAILED BOTANICAL DESCRIPTION

The aforementioned photographs and following observations and measurements describe plants grown during the winter and early spring in 12-cm containers in a glass-covered greenhouse in Bleiswijk, The Netherlands and grown under cultural practices typically used in commercial *Phalaenopsis* production. Plants were 18 months old when the photographs and description were taken. During the first 14 months of production of the plants, day and night temperatures averaged 28.5° C., and during the last four months of production of the plants, day and night temperatures averaged 20° C. Throughout the production of the plants, light levels ranged from 100μol to 180μol. In the following description, color references are made to The Royal Horticultural Society Colour Chart, 2015 Edition, except where general terms of ordinary dictionary significance are used.

Botanical classification: *Phalaenopsis hybrida* 'PHA177551'.

Parentage:

*Female, or seed, parent.*—*Phalaenopsis hybrida* 'PHALHORDIN', disclosed in U.S. Plant Pat. No. 33,096.

*Male, or pollen, parent.*—Proprietary breeding selection of *Phalaenopsis hybrida* identified as code No. 07-000001-5280, not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically light green in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial; moderately vigorous growth habit and moderate growth rate.

*Plant height, substrate level to top of foliar plane.*—About 18.4 cm.

*Plant height, substrate level to top of floral plane.*—About 51.1 cm.

*Plant diameter or spread.*—About 43.4 cm.

Leaf description:

*Arrangement and quantity.*13 Distichous, simple; sessile; about four to six fully-developed leaves per plant.

*Length.*—About 19.2 cm.

*Width.*—About 7.5 cm.

*Aspect.*—Horizontal to slightly drooping.

*Shape.*—Obovate to elliptic-obovate; slightly carinate.

*Apex.*—Unequal obtuse.

*Base.*—Sheathing. Sheath length: About 1.9 cm. Sheath width: About 1.4 cm. Sheath color: Close to 145A.

*Margin.*—Entire; not undulate.

*Texture and luster, upper surface.*—Smooth, glabrous; slightly glossy.

*Texture and luster, lower surface.*—Smooth, glabrous; moderately glossy.

*Venation pattern.*—Camptodromous.

*Color.*—Developing leaves, upper surface: Close to a blend of 143A and 146A; narrow marginal edges, close to 144A. Developing leaves, lower surface: Close to 144A. Fully expanded leaves, upper surface: Close to 146A; narrow marginal edges, close to 144A; venation, close to NN137B. Fully expanded leaves, lower surface: Close to 144A; venation, close to 143A.

Inflorescence description:

*Appearance and flowering habit.*—Showy zygomorphic flowers arranged on axillary simple or branched racemes; typically two inflorescences develop per plant; each inflorescence with about twelve flowers; flowers face outwardly on upright to outwardly arching inflorescences supported by upright peduncles; flowers with three petals, two lateral petals and one center petal transformed into a labellum and three sepals.

*Fragrance.*—None detected.

*Time to flower.*—Plants begin flowering about four months after planting; plants flower naturally during the winter into the spring.

*Flower longevity.*—Long flowering period, individual inflorescences maintain good substance for about 13 weeks on the plant; flowers not persistent.

*Inflorescence length (lowermost flower to inflorescence apex).*—About 26.8 cm.

*Inflorescence width.*—About 15.8 cm.

*Flower buds.*—Height: About 2 cm. Diameter: About 1.4 cm by 1.6 cm. Shape: Broadly ovate. Color: Close to a blend of 144C and 145A; towards the apex, close to 144C.

*Flower size.*—About 9.4 cm (vertical) by 10.2 cm (horizontal).

*Flower depth.*—About 2.7 cm.

*Petals, quantity and arrangement.*—Three, two lateral petals and one center petal transformed into a labellum.

*Lateral petals.*—Length: About 4.9 cm. Width: About 6.3 cm. Shape: Broadly reniform to close to broadly lunate. Apex: Obtuse to shallow and broad retuse. Margin: Entire; not undulate. Texture and luster, upper and lower surfaces: Smooth, glabrous; moderately velvety; matte. Color: When opening, upper surface: Close to a blend of 155C and NN155B; towards the apex and margins, close to NN155D. When opening, lower surface: Close to 155C; towards the apex and margins, close to NN155C; towards the base, close to 157D. Fully opened, upper and lower surfaces: Close to NN155D; color does not change with subsequent development.

*Labella.*—Appearance: Three-parted with two lateral lobes and a central lobe; overall shape, broadly cordate to reniform. Length, lateral lobes: About 2.3 cm. Width, lateral lobes: About 1.9 cm. Length, central lobe: About 2.1 cm. Width, central lobe: About 6 mm to 30 mm. Length, cirrhose tips: About 2 cm. Shape, lateral lobes: Broadly obovate. Shape, central lobe: Deltoid to kite-shaped with a slightly elongated apex. Apex, lateral lobes: Obtuse. Apex, central lobe: Narrowly acute and pointing downward. Margins, lateral and central lobes: Entire. Texture and luster, lateral and central lobes, upper and lower surfaces: Smooth, glabrous; moderately velvety; matte. Callosities: Located at the base of the labellum and attachment point of the lateral petals; about 5 mm in length, about 7 mm in width and about 6 mm in height. Color: When opening, upper surface: Lateral lobes: Close to NN155D; lower margins, close to 4A; at the base, axial stripes, close to 181B and 185B. Central lobe: Close to NN155C; towards the base, close to 2B; narrow marginal edges, close to 164B; at the base, close to NN155A with radial stripes, close to 181B; midvein, close to 12B; cirrhose apices, close to 1B. Callosities: Close to NN155A; at the apex, close to 4D with fine dots and stripes, close to 180C. When opening, lower surface. Lateral lobes: Close to NN155D; towards the base, close to N155A; lower margins, close to 4A. Central lobe: Close to NN155C; towards the base, close to 1B; narrow marginal edges, close to 164B; at the base, close to NN155A; midvein, close to 155C; cirrhose apices, close to 1B. Fully opened, upper surface: Lateral lobes: Close to NN155D; lower margins, close to 7B; at the base, axial stripes, close to 185B. Central lobe: Close to NN155D; towards the base, close to 3B; narrow marginal edges, close to 164B; at the base, close to NN155A with radial stripes, close to 181A; midvein, close to 11A; cirrhose apices, close to 7B. Callosities: Close to NN155A; at the apex, close to 5D with fine dots and stripes, close to 180B and 180C. Fully opened, lower surface: Lateral lobes: Close to NN155D; towards the base, close to N155A; lower margins, close to 7B. Central lobe: Close to NN155D; towards the base, close to 2B; narrow marginal edges, close to 164B; at the base, close to NN155C; cirrhose apices, close to 7B.

*Sepals.*—Quantity and arrangement: Three, one upper dorsal sepal and two lower lateral sepals. Length, dorsal sepal: About 5 cm. Width, dorsal sepal: About 3.5 cm. Length, lateral sepals: About 5.1 cm. Width, lateral sepals: About 3.2 cm. Shape, dorsal sepal: Ovate to elliptic-oblong. Shape, lateral sepals: Ovate. Apex, dorsal and lateral sepals: Bluntly acute. Base, dorsal and lateral sepals: Cuneate. Margins, dorsal and lateral sepals: Entire; not undulate. Texture and luster, dorsal and lateral sepals, upper and lower surfaces: Smooth, glabrous; moderately velvety; matte. Color, dorsal sepal: When opening, upper surface: Close to a blend of 155C and 157D. When opening, lower surface: Close to 145C; towards the apex and margins, close to 150D. Fully opened, upper surface: Close to NN155B. Fully opened, lower surface: Close to 157C; towards the apex and margins, close to NN155D. Color, lateral sepals: When opening, upper surface: Close to 157C; towards the base, close to a blend of 145C and 150C. When opening, lower surface: Close to a blend of 145C and 145D; towards the base, close to 145C; midvein, close to 150C. Fully opened, upper surface: Close to NN155B; towards the apex, close to NN155C; at the base, close to 157C. Fully opened, lower surface: Close to a blend of 145D and 150D; towards the apex and margins, close to NN155B and NN155C; venation, close to 150C.

*Peduncles.*—Length: About 62.2 cm. Diameter: About 6 mm. Strength: Strong. Aspect: Upright to outwardly arching. Texture and luster: Smooth, glabrous; matte. Color: Close to a blend of 143C and 144A with dense fine dots, close to 145D.

*Pedicels.*—Length: About 4.5 cm. Diameter: About 4 mm. Strength: Moderately strong. Aspect: About 45° from peduncle axis. Texture and luster: Smooth, glabrous; matte. Color: Close to 144C; distal end, close to 150C; proximal end, close to 144A.

*Reproductive organs.*—Androecium: Column length: About 9 mm. Column width: About 6 mm. Column color: Close to NN155C. Pollinia quantity: Two. Pollinia diameter (per two pollinia): About 2.5 mm. Pollinia color: Close to 23A. Gynoecium: Stigma length: About 3 mm. Stigma width: About 5 mm. Stigma shape: Reniform. Stigma color: Close to 155C. Ovary length: About 6 mm. Ovary diameter: About 1 mm. Ovary color: Close to 149C. Seeds and fruits: To date, seed and fruit development have not been observed on plants of the new *Phalaenopsis*.

Pathogen & Pest Resistance: To date, plants of the new *Phalaenopsis* have not been shown to be resistant to pathogens and pests common to *Phalaenopsis* plants.

Temperature Tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA177551' as herein illustrated and described.

* * * * *